United States Patent
Saga et al.

[11] Patent Number: 5,962,005
[45] Date of Patent: Oct. 5, 1999

[54] TRANSPARENT CELLULOSE HYDROGEL AND PRODUCTION PROCESS THEREOF

[75] Inventors: Hiroshi Saga; Hidenao Saito, both of Fukui, Japan

[73] Assignee: Rengo Co., Ltd, Osaka, Japan

[21] Appl. No.: 09/060,332

[22] Filed: Apr. 15, 1998

[30] Foreign Application Priority Data

Apr. 17, 1997 [JP] Japan ..................... 9-100159

[51] Int. Cl.$^6$ .............. B01J 13/00; A61F 2/14
[52] U.S. Cl. .......... 424/424; 424/426; 424/427; 424/428; 106/162.6; 106/163.01; 106/166.01; 106/167.01; 523/105; 523/106; 210/500.1; 210/500.21; 210/500.27; 210/500.29; 351/159; 351/160 R; 351/160 H
[58] Field of Search ................ 424/424, 426, 424/427, 428; 106/162.1, 162.6, 163.01, 166.01, 167.01; 523/105, 106; 210/500.1, 500.21, 500.27, 500.29; 351/159, 160 R, 160 H

[56] References Cited

U.S. PATENT DOCUMENTS

| 4,129,640 | 12/1978 | Rodier | 264/187 |
| 4,173,613 | 11/1979 | Rodier | 264/187 |
| 4,323,627 | 4/1982 | Joh | 428/398 |
| 5,336,231 | 8/1994 | Adair | 606/148 |

FOREIGN PATENT DOCUMENTS

| 0198490 | 10/1986 | European Pat. Off. |
| WO92/17125 | 10/1992 | WIPO |

*Primary Examiner*—Nathan M. Nutter
*Attorney, Agent, or Firm*—Wenderoth, Lind & Ponack, L.L.P.

[57] ABSTRACT

A transparent cellulose hydrogel having a transmittance of visible light of not less than 70%/mm and a tensile strength of not less than 10 kg/cm$^2$, wherein the hydroxyl groups of cellulose constituting said hydrogel are not chemically crosslinked; and a process for producing a transparent cellulose hydrogel, comprising coagulation and regeneration of cellulose from a cellulose solution using an aqueous solution containing an organic solvent in a proportion of 20–95 wt %. The cellulose hydrogel of the present invention is useful as a raw material of an ophthalmic material, such as soft contact lens, artificial crystal lens, artificial cornea, artificial vitreous body and the like, a carrier of fragrance, and a base of gel and cream, and the like. In addition, the transparent cellulose hydrogel of the present invention has a densely packed and uniform structure, so that it can provide a material of a separation membrane having a small molecular cutoff and high pressure resistance.

6 Claims, No Drawings

TRANSPARENT CELLULOSE HYDROGEL AND PRODUCTION PROCESS THEREOF

TECHNICAL FIELD OF THE INVENTION

The present invention relates to a transparent cellulose hydrogel and a process for production thereof. More particularly, the present invention relates to a transparent cellulose hydrogel useful as a raw material of an ophthalmic material, such as soft contact lens, artificial crystal lens, artificial cornea, artificial vitreous body and the like, a carrier of fragrance, a base of gel and cream, a material of separation membranes such as an ultrafiltration membrane and a dialysis membrane, and the like, and to a production process thereof.

BACKGROUND OF THE INVENTION

Cellulose occurs naturally and has a high hydrophilicity. Thus, a hydrogel composed of this cellulose has superior biodegradability and biocompatibility, and has been widely used in various fields of food, cosmetics, medical supplies and the like. In addition, a transparent hydrogel material for soft contact lenses has been recently developed using a cellulose hydrogel.

Conventionally, various acrylate derivatives having a hydroxyl group have been used as a raw material of hydrated soft contact lenses. Of such derivatives, poly(2-hydroxyethyl methacrylate) (PHEMA) has been most often used in view of the relatively superior transparency and machinability. What influences the performance of a soft contact lens most is oxygen permeability coefficient. In the case of a hydrated soft contact lens, an increased water content can raise the oxygen permeability coefficient. However, PHEMA hydrogel achieves only about 38% water content.

This became an incentive for the development of a cellulose hydrogel having a high water content by itself. In general, however, a cellulose hydrogel has insufficient transparency due to radical swelling and shrinkage during coagulation and regeneration of cellulose. In addition, a gel having a high water content tends to show insufficient mechanical strength.

Thus, there have been made various attempts to solve these problems and to provide, from cellulose, a highly hydrated hydrogel superior in transparency and having a high strength. For example, a hydrogel crosslinked using a crosslinking agent has been proposed (Japanese Patent Unexamined Publication Nos. 2-168958 and 5-237142). In both cases, however, the use of a crosslinking agent for chemical crosslinking poses a possible problem of effusion of the crosslinking agent and side reaction in the gel to change physical properties of the gel such as a decrease in the transparency.

As explained in the above, the cellulose hydrogel is associated with difficulty in handling of the gel and cannot be used with ease, which consequently resulted in a failure to provide a gel applicable to various uses. In the case of a cellulose hydrogel, moreover, one wherein the hydroxyl groups of cellulose constituting the gel are not chemically crosslinked, and which satisfies requirements in terms of transparency and mechanical strength has not been found.

The cellulosic materials have been typically used in water treatment and food processing, as well as recovery of valuable components such as medicines from microorganisms and culture media and the like, as a separation membrane such as an ultrafiltration membrane and a dialysis membrane. When a cellulose solution is cast into a film and the film is coagulated and regenerated without further treatment, the size of the pores formed in the membrane shows very wide distribution, which in turn leads to greater molecular cutoff to result in inefficient separation of the desired substance. The wider pore size distribution also brings about non-uniform structure of the membrane, causing low mechanical strength and a failure to separate under a high pressure. In addition, an attempt has been made to reduce the molecular cutoff and increase mechanical strength by drawing or crosslinking a cellulose membrane (see, for example, Japanese Patent Unexamined Publication No. 3-65224). Such method requires additional steps of drawing and crosslinking to ultimately complicate the production process.

It is therefore an object of the present invention to provide a transparent cellulose hydrogel having a densely packed and uniform structure, as well as superior transparency and mechanical strength, wherein the hydroxyl groups of cellulose constituting the gel are not chemically crosslinked, and a process thereof.

SUMMARY OF THE INVENTION

According to the present invention, it has now been found that the objects of the present invention can be accomplished by the use of a specific solvent for the coagulation and regeneration of cellulose, which avoids degradation of transparency caused by the occurrence of strains due to radical swelling and shrinkage during coagulation and regeneration of cellulose. Thus, the inventive transparent cellulose hydrogel has a densely packed uniform structure even without chemical crosslinking with a crosslinking agent and is superior in transparency and mechanical strength, so that it is free of effusion of a crosslinking agent, side reaction or increased production steps. In consequence, it is useful as a raw material of an ophthalmic material, such as soft contact lens, artificial crystal lens, artificial cornea, artificial vitreous body and the like, a carrier of fragrance, and a base of gel and cream, and the like.

In the present invention, the "densely packed and uniform structure" means a structure having many pores and narrow pore size distribution. When such a gel having a densely packed and uniform structure is used as a separation membrane, sufficient amount can be treated even if the molecular cutoff is small, thereby attaining an efficient separation of a solute. Thus, the inventive cellulose hydrogel can be used as a separation membrane such as an ultrafiltration membrane and a dialysis membrane.

That is, the present invention provides the following.

(1) A transparent cellulose hydrogel having a transmittance of visible light of not less than 70%/mm and a tensile strength of not less than 10 kg/cm$^2$, wherein the hydroxyl groups of cellulose constituting said hydrogel are not chemically crosslinked.

(2) The transparent cellulose hydrogel of (1) above, which is a raw material of an ophthalmic material.

(3) The transparent cellulose hydrogel of (2) above, wherein the ophthalmic material is a soft contact lens.

(4) The transparent cellulose hydrogel of (1) above, which is a material of a separation membrane.

(5) A process for producing a transparent cellulose hydrogel, comprising coagulation and regeneration of cellulose from a cellulose solution using an aqueous solution containing an organic solvent in a proportion of 20–95 wt %.

(6) The process of (5) above, wherein the cellulose solution is a viscose and the aqueous solution contains the organic solvent in a proportion of 50–95 wt % and said aqueous solution contains a decomposition agent of a cellulose xanthate.

DETAILED DESCRIPTION OF THE INVENTION

The transparent cellulose hydrogel of the present invention comprises cellulose having hydroxyl groups that are not chemically crosslinked.

The hydroxyl groups which are not chemically crosslinked means that the hydroxy groups of cellulose are not chemically crosslinked by various crosslinking agents, and the gel is formed by physical crosslinking by the hydrogen bonding between the hydroxyl groups in cellulose.

In addition, the transparent cellulose hydrogel of the present invention has a transmittance of visible light of not less than 70%/mm.

When the transmittance of visible light is less than 70%/mm, the gel becomes apparently turbid, making its use as a transparent material difficult. The transmittance is preferably not less than 80%/mm.

In the present invention, the transmittance of visible light refers to the transmittance of visible light of a filmlike gel at a wavelength of 550 nm as measured in water at 25° C. using a spectrophotometer, which has been converted to a transmittance of visible light per 1 mm thickness of gel.

This transmittance of visible light can be controlled by the kind, concentration and the like of the organic solvent contained in an aqueous organic solvent solution used for the production of the cellulose hydrogel.

Moreover, the transparent cellulose hydrogel of the present invention has a tensile strength of not less than 10 kg/cm$^2$.

When the tensile strength is less than 10 kg/cm$^2$, the gel handling property becomes unpractically poor. It is preferably not less than 15 kg/cm$^2$.

In the present invention, the tensile strength was measured as in the following. That is, excessive water on the surface of a gel is wiped with a filter paper, the gel is punched out into a No. 1 (½) dumb-bell shape with a sample punch according to JIS K 7113 and the tensile strength of said swollen test piece is measured under the conditions of tensile speed of 50.0 mm/min and temperature of 20° C. by a universal testing machine.

Said tensile strength is controlled by the kind and concentration of organic solvent contained in the aqueous organic solvent solution to be used for the production of cellulose hydrogel, polymerization degree of cellulose, concentration of the cellulose solution and the like.

The inventive transparent cellulose hydrogel as mentioned above can be preferably obtained by a process comprising coagulation and regeneration of cellulose from a cellulose solution using an aqueous solution containing an organic solvent. For example, cellulose can be coagulated and regenerated by immersing a gel formed in a desired shape from a cellulose solution, in an aqueous solution containing an organic solvent.

This cellulose solution is an aqueous or organic solvent solution containing cellulose, a derivative thereof (e.g., cellulose xanthate) or a complex thereof (e.g., cellulose cuprammonium complex) and subject to no particular limitation as long as it can coagulate and cellulose can be regenerated from said solution.

To be specific, examples of the aqueous cellulose solution include a viscose obtained by dissolving sodium cellulose xanthate in an aqueous alkali solution and one obtained by dissolving cellulose in a cuprammonium solution (schweizer's reagent). Examples of the organic solvent type cellulose solution include those obtained by dissolving cellulose in dimethyl sulfoxide/paraformaldehyde, dimethylformamide/nitrogen tetraoxide, dimethylformamide/chloral, N,N-dimethylacetamide/lithium chloride and the like. Of these, viscose is preferable for the reasons that it is produced in large amounts, is economical, is readily available and is relatively stable.

The cellulose source to be used for said cellulose solution preferably shows a polymerization degree of approximately 100–2,000, more preferably 200–1,000, in view of the handling of the solution and mechanical strength of the gel. When it has a low polymerization degree, the gel shows poor mechanical strength, but when it has a high polymerization degree, the solution is caused to have a high viscosity, resulting in poor handling property.

While the cellulose concentration of said cellulose solution varies depending on the solvent to be used, it is generally 3–15 wt %, preferably 5–10 wt %. When it is less than 3 wt %, the mechanical strength of the gel tends to decrease, while when it exceeds 15 wt %, the viscosity of the cellulose solution is extremely high and as a consequence the handling of the solution frequently becomes difficult, though subject to variation depending on the kind of cellulose solution to be used.

The cellulose solution has a viscosity of generally 50–500,000 cP, preferably 100–200,000 cP, at 20° C., in view of the handling of the solution and mechanical strength of the gel.

In the present invention, the viscosity is measured by a Brookfield viscometer at 20° C. The polymerization degree of cellulose to be used and cellulose concentration can control this viscosity.

When a viscose is used as a cellulose solution, for example, a viscose used for producing cellophane can be employed. This viscose generally has the following properties; cellulose concentration of 3–15 wt %, preferably 4–10 wt %, ammonium chloride value of 3–12, preferably 4–9, and alkali (sodium hydroxide) concentration of 2–15 wt %, preferably 5–13 wt %. The viscosity of the viscose at 20° C. is 50–100,000 cP, preferably 100–50,000 cP.

The aqueous solution containing an organic solvent to be used in the process for producing the transparent cellulose hydrogel of the present invention is not particularly limited as long as the organic solvent used here shows high hydrophilicity and is readily miscible with water. Examples of the organic solvent include methanol, ethanol, acetonitrile, isopropyl alcohol, acetone, n-propyl alcohol, tetrahydrofuran and the like.

The transparent cellulose hydrogel of the present invention having a densely packed and uniform structure and superior transparency and mechanical properties can be obtained by the use of such aqueous solution containing an organic solvent which makes it possible to coagulate and regenerate cellulose while performing and balancing the two inconsistent actions of gel shrinkage caused by dehydration due to the organic solvent and swelling with water.

While the organic solvent content varies depending on the kind of cellulose solution and organic solvent to be used, it is generally 20–95 wt %, preferably 30–90 wt %, of the aqueous solution containing the organic solvent. When the content is less than 20 wt %, the gel is caused to swell and the resulting gel becomes turbid and the mechanical strength of the gel is degraded. With increasing organic solvent contents of the aqueous solution, however, the gel has smaller volumes due to a greater action of shrinkage, thus resulting in more densely packed structures, which in turn increases transparency and mechanical strength of the gel. On the other hand, when it exceeds 95 wt %, the shrinkage becomes pronounced and resultant great strains in the gel cause lower transparency and less mechanical strength. Thus, when the organic solvent content of the aqueous organic solvent solution is within the range of 20–95 wt %, the gel has a densely packed and uniform structure in the entirety thereof.

In particular, when a viscose is used as the cellulose solution, said aqueous solution has an organic solvent content of preferably 50–95 wt %, more preferably 60–90 wt %. When the content is less than 50 wt %, a transparent gel cannot be formed easily and the gel tends to have lower mechanical strength. On the other hand, when it exceeds 95 wt %, the transparency and mechanical strength tend to decrease.

When the cellulose dissolved in a cellulose solution is a derivative or complex thereof, such derivative or complex needs to be decomposed to regenerate cellulose. Thus, a decomposing agent of the cellulose derivative or complex needs to be added to the aqueous solution in an amount sufficient to maintain a suitable coagulation rate of the cellulose solution.

The decomposing agent of the cellulose derivative or complex may be one known per se, which is, for example, an inorganic acid (e.g., sulfuric acid, hydrochloric acid and phosphoric acid) or an organic acid (e.g., acetic acid) when the cellulose solution is a viscose. These may be used alone or in combination.

The amount of the decomposing agent varies depending on the kind of cellulose solution and decomposing agent to be used. For example, when hydrochloric acid is used as the decomposing agent of a viscose, it is added to an aqueous solution containing an organic solvent to a concentration of generally 0.02–1N, preferably 0.05–0.5N.

When it is less than 0.02N, cellulose hydrogel cannot retain its shape during coagulation and regeneration or substitution by water, thereby losing the mechanical strength, whereas when it exceeds 1N, the transparency of the gel may be degraded.

In contrast, when a cellulose solution, wherein the cellulose itself is dissolved, is used, such as an organic solvent type cellulose solution, a decomposing agent is not necessary.

Subsequent to the above step of coagulation and regeneration of cellulose from a cellulose solution using an aqueous solution containing an organic solvent, the aqueous solution is substituted with water to give a cellulose hydrogel.

This substitution with water can be carried out by a method known per se, such as washing with running water or repeatedly immersing the gel in fresh water.

The transparent cellulose hydrogel of the present invention thus obtained is superior in transparency and mechanical strength. It is free of effusion of a crosslinking agent or side reaction caused thereby, since chemical crosslinking using a crosslinking agent is not applied, or of additional process. Therefore, the transparent cellulose hydrogel of the present invention is useful as a raw material of an ophthalmic material, such as soft contact lens, artificial crystal lens, artificial cornea, artificial vitreous body and the like, a carrier of fragrance, and a base of gel and cream, and the like. In addition, the transparent cellulose hydrogel of the present invention has a densely packed and uniform structure, so that it is also useful as a material of a separation membrane such as an ultrafiltration membrane and a dialysis membrane.

The present invention is explained in more detail by way of Examples, to which the present invention is not limited.

The properties in the Examples were measured in the following manner.

Transmittance of visible light

Using a spectrophotometer, the transmittance of visible light at a wavelength of 550 nm was measured. Using a filmlike gel as a sample, the measurement was carried out in water at 25°0 C. and the resulting value was converted to the transmittance of visible light per 1 mm thickness of gel.

Tensile strength

Excessive water on the surface of a gel was wiped with a filter paper, and the gel was punched out in a No. 1 (½) dumb-bell shape with a sample punch according to JIS K 7113 and the tensile strength of said swollen test piece was measured using a universal testing machine Shimadzu Autograph AGS-100G under the conditions of tensile speed of 50.0 mm/min and temperature of 20° C.

Water content

The water content of a gel was calculated from the following formula:

[(weight of wet gel−weight of dried gel)/weight of wet gel]×100

Note that the weight of wet gel was weighed after wiping excessive water on the surface of the sample, and the weight of dried gel was weighed after drying the sample in a drying oven at 105° C. until it reached a constant weight.

Some samples were measured for permeate flux and molecular cutoff which are indices to show performance of separation membrane.

Permeate flux

A hydrogel membrane was set on an ultrafilter Advantec UHP-62K, and pure water was filled above the membrane. The amount of pure water passing through the filter in one hour under a pressure of 4 kgf/cm$^2$ applied with nitrogen was measured and taken as the value of permeate flux.

Molecular cutoff

In the same manner as in the above measurement of permeate flux except that, instead of pure water, several kinds of solutions containing dextran having a different molecular weight (molecular weight: 10,000–2,000,000) as a solute were passed through hydrogel membranes, the measurement was performed. The rejection percentage was calculated from the solute concentrations of the permeate and concentrate, and the value corresponding to 90% rejection on the graph plotted according to respective molecular weights was taken as the molecular cutoff.

Rejection (%)=(1−permeate concentration/concentrate concentration)×100

Protein adsorption tests were performed for some samples. Protein adsorption property is one of the indices to show the possibility of utility as a soft contact lens.

Protein adsorption test

A sample gel was immersed in a phosphate buffer (pH=7.3) containing 1 wt % γ-globulin, bovine serum albumin or lysozyme at 24° C. for 24 hr to allow adsorption of the protein. This gel was once washed with a phosphate buffer, and immersed in an aqueous solution containing 1 wt % sodium dodecyl sulfate and 1 wt % sodium carbonate at 24° C. for 24 hr to extract the adsorbed protein. A BCA reagent (Pierce) was added to this extract and the mixture was shaken at 60° C. for 1 hr to develop color, followed by measurement of absorbance at 562 nm. The amount of the protein was determined based on the previously determined calibration curves of γ-globulin, bovine serum albumin and lysozyme, and the obtained values were expressed in the adsorption per 1 cm$^2$.

The PHEMA gel used for comparison was obtained by adding azobisisobutyronitrile as a polymerization initiator and methylenebisacrylamide as a crosslinking agent to HEMA (2-hydroxyethyl methacrylate), exposing the mixture to ultraviolet rays for polymerization and washing the resulting gel thoroughly with water. The PVA gel was prepared by dissolving PVA in a mixed solvent of DMSO and water with stirring at 120° C. for 30 min, freezing the dissolved product placed in a mold overnight at −20° C. and then raising the temperature gradually to room temperature, thereby thawing same, and washing the gel with running water.

EXAMPLE 1

A viscose (cellulose concentration 9.5 wt %, ammonium chloride value 6, alkali concentration 6 wt %, viscosity 5,500 cP) for producing cellophane was cast on a glass plate in a thickness of 1 mm and coagulated and regenerated with an aqueous HCl-acetone solution (solution adjusted to have an HCl concentration of 0.2N, a mixed solvent of acetone 80 wt %+water 20 wt %). Washing same with running water gave transparent and highly strong cellulose hydrogel (transmittance of visible light: 82.3%/mm, tensile strength: 115 kg/cm$^2$, water content: 64.4%).

EXAMPLE 2

In the same manner as in Example 1 except that the HCl concentration of the aqueous HCl-acetone solution was adjusted to 0.5N, a transparent and highly strong cellulose hydrogel (transmittance of visible light: 72.9%/mm, tensile strength: 87.9 kg/cm$^2$, water content: 66.8%) was obtained.

This gel (membrane thickness 470 μm) was measured for permeate flux and molecular cutoff. As a result, the molecular cutoff was 300,000 and permeate flux was 1.9 l/m$^2$ hr.

EXAMPLE 3

In the same manner as in Example 1 except that an aqueous HCl-methanol solution (solution adjusted to have an HCl concentration of 0.2N, a mixed solvent of methanol 80 wt %+water 20 wt %) was used instead of the aqueous HCl-acetone solution, a transparent and highly strong cellulose hydrogel (transmittance of visible light: 80.6%/mm, tensile strength: 56.0 kg/cm$^2$, water content: 73.3%) was obtained.

EXAMPLE 4

In the same manner as in Example 1 except that a solution (cellulose concentration 4.0wt %, viscosity 46,000 cP) obtained by dissolving pulp in dimethyl sulfoxide solution containing 35 wt % tetraethylammonium chloride was used instead of the viscose and an aqueous acetone solution having an acetone concentration of 60wt % was used instead of the aqueous HCl-acetone solution, a transparent and highly strong cellulose hydrogel (transmittance of visible light: 71.7%/mm, tensile strength: 12.5 kg/cm$^2$, water content: 80.4%) was obtained.

EXAMPLE 5

In the same manner as in Example 1 except that a solution (cellulose concentration 7.0 wt %, viscosity 21,000 cP) obtained by dissolving cellulose powder CF11 (Whatman) in an N,N-dimethylacetamide solution containing 10 wt % lithium chloride was used instead of the viscose and an aqueous acetone solution having an acetone concentration of 65 wt % was used instead of the aqueous HCl-acetone solution, a transparent and highly strong cellulose hydrogel (transmittance of visible light: 97.4%/mm, tensile strength: 14.9 kg/cm$^2$, water content: 81.8%) was obtained.

This cellulose hydrogel was measured for protein adsorption. As a result, γ-globulin was 38 ng/cm$^2$, bovine serum albumin was 27 ng/cm$^2$ and lysozyme was 202 ng/cm$^2$. These values were as low as those of PHEMA gel (γ-globulin: 139 ng/cm$^2$, bovine serum albumin: 59 ng/cm$^2$ and lysozyme: 416 ng/cm$^2$) and PVA gel (γ-globulin: 31 ng/cm$^2$, bovine serum albumin: 39 ng/cm$^2$ and lysozyme: 136 ng/cm$^2$).

EXAMPLE 6

In the same manner as in Example 5 except that an aqueous acetone solution having an acetone concentration of 40 wt % was used instead of the aqueous acetone solution having an acetone concentration of 65 wt %, a transparent and highly strong cellulose hydrogel (transmittance of visible light: 96.6%/mm, tensile strength: 11.8 kg/cm$^2$, water content: 82.7%) was obtained.

EXAMPLE 7

In the same manner as in Example 5 except that an aqueous acetone solution having an acetone concentration of 90 wt % was used instead of the aqueous acetone solution having an acetone concentration of 65 wt %, a transparent and highly strong cellulose hydrogel (transmittance of visible light: 92.8%/mm, tensile strength: 13.8 kg/cm$^2$, water content: 80.9%) was obtained.

Comparative Example 1

In the same manner as in Example 1 except that a 0.2N aqueous HCl solution was used instead of the aqueous HCl-acetone solution, a cellulose hydrogel (transmittance of visible light: 31.8%/mm, tensile strength: 7.4 kg/cm$^2$, water content: 79.9/%) was obtained. The obtained cellulose hydrogel was turbid and less strong.

This gel was measured for permeate flux and molecular cutoff. However, the membrane had less strength and became broken when a load of about 2 kgf/cm$^2$ was applied.

Comparative Example 2

In the same manner as in Example 1 except that a 1.0N aqueous HCl solution was used instead of the aqueous HCl-acetone solution, a cellulose hydrogel (transmittance of visible light: 23.6%/mm, tensile strength: 9.2 kg/cm$^2$, water content: 80.8%) was obtained. The obtained cellulose hydrogel was turbid.

This gel (membrane thickness 650 μm) was measured for permeate flux and molecular cutoff. As a result, permeate flux was as great as 20.3 l/m$^2$ hr and molecular cutoff was 1,000,000,000, which value being unsuitable for a separation membrane.

Comparative Example 3

In the same manner as in Example 4 except that acetone was used instead of the aqueous acetone solution having an acetone concentration of 60 wt %, a cellulose hydrogel (transmittance of visible light: 34.2%/mm, tensile strength: 15.6 kg/cm$^2$, water content: 74.8%) was obtained. The obtained cellulose hydrogel was turbid.

Comparative Example 4

In the same manner as in Example 5 except that water was used instead of the aqueous acetone solution having an acetone concentration of 65 wt %, a cellulose hydrogel (transmittance of visible light: 73.1%/mm, tensile strength: 4.0 kg/cm$^2$, water content: 85.2%) was obtained. The obtained cellulose hydrogel was transparent but weak.

According to the present invention, a cellulose hydrogel having superior transparency and mechanical strength, as well as high water content, can be provided even without chemical crosslinking of cellulose constituting the cellulose hydrogel with a crosslinking g agent. Such cellulose hydrogel is useful as a raw material of an ophthalmic material, such as soft contact lens, artificial crystal lens, artificial cornea, artificial vitreous body and the like, a carrier of fragrance, and a base of gel and cream, and the like. In addition, the transparent cellulose hydrogel of the present invention has a densely packed and uniform structure, so that it can provide a material of a separation membrane having a small molecular cutoff and high pressure resistance.

This application is based on application No. 100159/1997 filed in Japan, the content of which is incorporated hereinto by reference.

What is claimed is:

1. A transparent cellulose hydrogel having a transmittance of visible light of not less than 70%/mm and a tensile strength of not less than 10 kg/cm$^2$, wherein all of the hydroxyl groups of cellulose constituting said hydrogel are not chemically crosslinked.

2. An ophthalmic material comprising the transparent cellulose hydrogel of claim 1 as a raw material.

3. The ophthalmic material of claim 2, which is a soft contact lens.

4. A separation membrane comprising the transparent cellulose hydrogel of claim 1.

5. A process for producing a transparent cellulose hydrogel, comprising coagulation and regeneration of cellulose from a cellulose solution using an aqueous solution containing at least one organic solvent selected from the group consisting of methanol, ethanol, acetonitrile, isopropyl alcohol, acetone, n-propyl alcohol and tetrahydrofuran, in a proportion of 30–90 wt % based on the weight of the aqueous solution.

6. A process for producing a transparent cellulose hydrogel, comprising coagulation and regeneration of cellulose from a viscose using an aqueous solution containing an organic solvent, which is a non-solvent for cellulose and is miscible with water, in a proportion of 50–95 wt % based on the weight of the aqueous solution, said aqueous solution containing a decomposition agent which decomposes cellulose xanthate into cellulose.

* * * * *